(12) United States Patent
Grover et al.

(10) Patent No.: US 10,918,521 B2
(45) Date of Patent: *Feb. 16, 2021

(54) METHOD AND APPARATUS FOR TREATING AN OCULAR DISORDER

(71) Applicant: INNOVATIVE GLAUCOMA SOLUTIONS, LLC, Dallas, TX (US)

(72) Inventors: Davinder S. Grover, Dallas, TX (US); David G. Godfrey, Dallas, TX (US); Ronald L. Fellman, Dallas, TX (US)

(73) Assignee: INNOVATIVE GLAUCOMA SOLUTIONS, LLC, Dallas, TX (US)

( * ) Notice: Subject to any disclaimer, the term of this patent is extended or adjusted under 35 U.S.C. 154(b) by 72 days.

This patent is subject to a terminal disclaimer.

(21) Appl. No.: 15/966,282

(22) Filed: Apr. 30, 2018

(65) Prior Publication Data

US 2018/0243135 A1  Aug. 30, 2018

Related U.S. Application Data

(63) Continuation of application No. 14/376,235, filed as application No. PCT/US2012/062332 on Oct. 27, 2012, now Pat. No. 9,956,116.

(60) Provisional application No. 61/594,502, filed on Feb. 3, 2012.

(51) Int. Cl.
| | |
|---|---|
| *A61F 9/00* | (2006.01) |
| *A61F 9/007* | (2006.01) |
| *A61B 5/06* | (2006.01) |
| *A61F 9/008* | (2006.01) |
| *A61F 9/013* | (2006.01) |

(52) U.S. Cl.
CPC .......... *A61F 9/00781* (2013.01); *A61B 5/065* (2013.01); *A61F 9/007* (2013.01); *A61F 9/0133* (2013.01); *A61F 2009/00861* (2013.01); *A61F 2009/00868* (2013.01); *A61F 2009/00885* (2013.01); *A61F 2009/00891* (2013.01)

(58) Field of Classification Search
CPC . A61F 9/0017; A61F 9/00736; A61F 9/00781
See application file for complete search history.

(56) References Cited

U.S. PATENT DOCUMENTS

| | | | |
|---|---|---|---|
| 8,545,430 B2 | 10/2013 | Silvestrini | |
| 9,956,116 B2 * | 5/2018 | Grover | ............... A61F 9/00781 |
| 2006/0149194 A1 | 7/2006 | Conston et al. | |
| 2006/0195187 A1 | 8/2006 | Stegmann et al. | |
| 2007/0073275 A1 | 3/2007 | Conston et al. | |

(Continued)

FOREIGN PATENT DOCUMENTS

WO    WO-2000/064389 A1    11/2000

OTHER PUBLICATIONS

Sarkisian, "An illuminated microcatheter for 360-degree trabeculotomy in congenital glaucoma: A retrospective case series article"; J. AAPOS; 2010; 14: 412-416.

*Primary Examiner* — Todd J Scherbel
(74) *Attorney, Agent, or Firm* — Winstead PC

(57) ABSTRACT

Embodiments of the claimed invention are directed to the treatment of glaucoma (or conditions of elevated intraocular pressure) using a novel ab interno trabeculotomy procedure that uses a flexible device. At least one advantage of the present method is that it does not require a conjunctival or scleral incision, which in turn improves patient recovery time and healing.

14 Claims, 2 Drawing Sheets

(56) References Cited

U.S. PATENT DOCUMENTS

| | | | |
|---|---|---|---|
| 2007/0276420 A1* | 11/2007 | Sorensen | A61B 17/320016 606/167 |
| 2009/0287143 A1 | 11/2009 | Line | |
| 2010/0234790 A1 | 9/2010 | Tu et al. | |
| 2011/0196487 A1* | 8/2011 | Badawi | A61F 9/0017 623/4.1 |
| 2011/0319806 A1 | 12/2011 | Wardle | |
| 2012/0303010 A1 | 11/2012 | Vijfvinkel | |

* cited by examiner

METHOD AND APPARATUS FOR TREATING AN OCULAR DISORDER

CROSS-REFERENCES TO RELATED APPLICATIONS

This application is a continuation of application Ser. No. 14/376,235 filed Aug. 1, 2014, which is a national stage (35 U.S.C. § 371) application of PCT/US2012/062332 filed Oct. 27, 2012, which claims priority to U.S. Provisional Application Ser. No. 61/594,502 filed on Feb. 3, 2012, all of which are incorporated herein by reference in their entirety.

FIELD OF THE INVENTION

The present invention generally relates to improved systems and methods for the reduction of elevated pressure in the human eye. More particularly, the present invention relates to the treatment of glaucoma by an ab interno method for trabeculotomy utilizing a device inserted into Schlemm's canal and advanced along Schlemm's canal.

BACKGROUND OF THE INVENTION

About two percent of the adult population in the United States has glaucoma. Glaucoma is a group of eye diseases that causes pathological changes in the optic disk and corresponding visual field loss resulting in blindness if untreated. Intraocular pressure elevation is the major etiologic factor in all glaucomas.

In most glaucomas the source of resistance to outflow is in the trabecular meshwork. The tissue of the trabecular meshwork allows the "aqueous" to enter Schlemm's canal, which then empties into aqueous collector channels in the posterior wall of Schlemm's canal and then into aqueous veins. The "aqueous" or aqueous humor is a transparent liquid that fills the region between the cornea at the front of the eye and the lens. The aqueous humor is constantly secreted by the ciliary body around the lens, and thus there is a continuous flow of the aqueous humor from the ciliary body to the eye's front chamber. The eye's pressure is determined by a balance between the production of aqueous and its exit through the trabecular meshwork (major route) or via uveoscleral outflow (minor route). The trabecular meshwork is located between the outer rim of the iris and the internal periphery of the cornea. The portion of the trabecular meshwork adjacent to Schlemm's canal causes most of the resistance to aqueous outflow (juxtacanalicular meshwork).

Glaucoma is grossly classified into two categories: closed-angle glaucoma and open-angle glaucoma. The closed-angle glaucoma is caused by closure of the anterior angle by contact between the iris and the inner surface of the trabecular meshwork. Closure of this anatomical angle prevents normal drainage of aqueous humor from the anterior chamber of the eye. Open-angle glaucoma is any glaucoma in which the angle of the anterior chamber remains open, but the exit of aqueous through the trabecular meshwork is diminished.

All current therapies for glaucoma are directed at decreasing intraocular pressure. This is initially done by medical therapy with drops or pills that reduce the production of aqueous humor or increase the outflow of aqueous. However, these various drug therapies for glaucoma are sometimes associated with significant side effects, such as headache, blurred vision, allergic reactions, and potential interactions with other drugs. When the drug therapy fails, surgical therapy is used. Surgical therapy for open-angle glaucoma consists of laser (trabeculoplasty), trabeculectomy and aqueous shunting implants after failure of trabeculectomy or if trabeculectomy is unlikely to succeed.

Trabeculectomy is a surgical procedure used in the treatment of glaucoma to relieve intraocular pressure by creating a pathway for aqueous from the anterior chamber to the sub-conjunctival space. It is the most common glaucoma surgery performed and creates a bypass route for the aqueous humor to drain aqueous humor from within the eye to underneath the conjunctiva where it is absorbed. Additionally, glaucoma drainage devices are also frequently used for the treatment of glaucoma. These devices utilize hardware and a tube to shunt aqueous humor from within the eye to underneath the conjunctiva. Both trabeculectomy and drainage device implantation requires dissection of the external sclera and conjunctiva of the eye.

All of the currently known and performed embodiments and variations of glaucoma surgery have numerous disadvantages and moderate success rates. These modalities are currently limited by wound healing processes at the site of surgery, which are further accelerated in cases that have undergone previous conjunctival or scleral surgery. The wound healing and scarring process associated with glaucoma surgery involving the conjunctiva and sclera also limits the ability to perform subsequent glaucoma surgery in the same location. Therefore, there is a great clinical need for the treatment of glaucoma by a method that would be faster, safer and less expensive than currently available modalities, which involve either substantial trauma to the eye and require great surgical skill by creating a hole over the full thickness of the sclera or cornea-scleral junction to create a flow path from the anterior chamber into the subconjunctival space or by placing a permanent device into the eye.

The morbidity associated with trabeculectomy consists of failure (10-15% per year), infection (a lifelong risk about 2-5%), choroidal hemorrhage (1%, a severe internal hemorrhage from pressure too low resulting in visual loss), cataract formation, and hypotony maculopathy (potential visual loss from pressure too low).

Thus, it would be desirable to develop a surgical system and method for treating glaucoma that does not require a conjunctival and scleral incision, which in turn would hasten patient healing and improve recovery time. Such a procedure would also spare the sclera and conjunctival tissues, allowing ab-externo surgery at a later date if needed.

SUMMARY OF THE INVENTION

Figure 1:
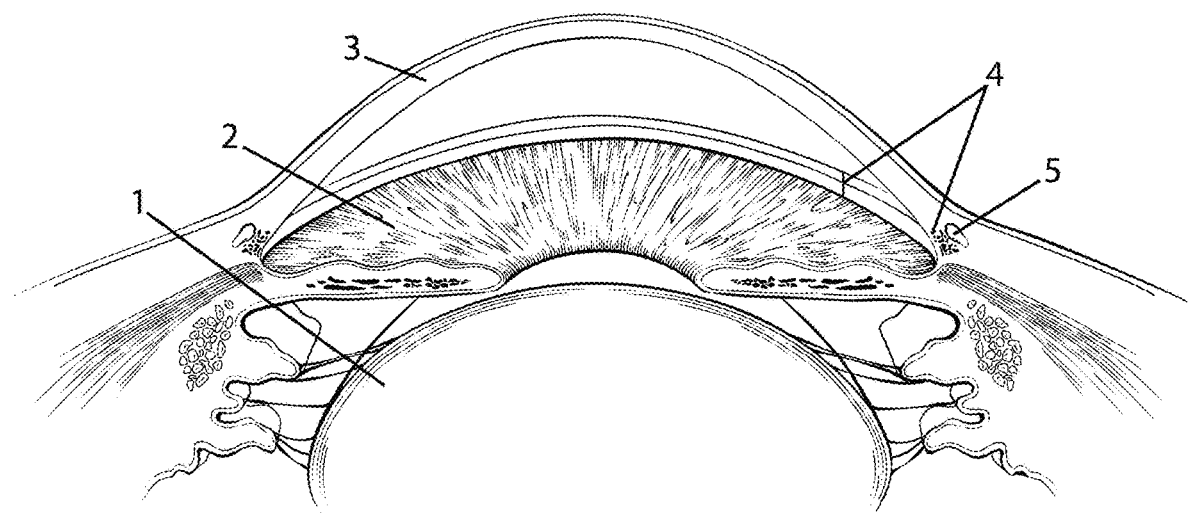
FIG. 1 shows the structure of an eye in cross-section and its various parts.

An embodiment of the invention is directed to an apparatus for treating an ocular disorder in a patient, the apparatus comprising a device, wherein said device comprises a body having a proximal section and a distal section, the body having a maximum cross-sectional dimension sized to allow insertion of the body through an opening in the eye; and a lumen extending through the body from the proximal section to the distal section, wherein the device is configured for ab interno insertion of the device through an opening in the eye and sized to extend into Schlemm's canal; and wherein said device has sufficient length between the proximal section and distal section such that, upon insertion, at least a portion of the proximal section of the microcatheter is disposed within Schlemm's canal and at least a portion of the distal section of the microcatheter extends into and along a portion of an outflow pathway of the eye.

A further embodiment of the invention is directed to a method for performing a trabeculotomy ab interno, the method comprising the steps of, making at least one corneal incision, placing a surgical instrument with a cutting edge through the corneal incision, making an incision into the trabecular meshwork to access the lumen of Schlemm's canal, placing the distal end of a device into the anterior chamber, advancing the device within Schlemm's canal, pulling the distal tip of the device into the anterior chamber, applying tension to the device within the canal by applying tension between the ends of the device within Schlemm's canal thereby rupturing the trabecular meshwork in the area cannulated by the device, and withdrawing the device through the corneal incision.

DETAILED DESCRIPTION OF EMBODIMENTS OF THE INVENTION

The 360-degree ab externo suture trabeculotomy has been the gold standard for the treatment of congenital glaucoma for the past several decades. This technique has also been used successfully in the treatment of juvenile open angle glaucoma as well as various other open angle glaucomas. In a 360-degree trabeculotomy, the goal of this procedure is to rupture or tear through the trabecular meshwork to open the entire length of Schlemm's canal to directly communicate with the anterior chamber, thereby removing the resistance to aqueous outflow of the trabecular meshwork and reducing intraocular pressure. This is accomplished by passing a device 360 degrees within Schlemm's canal. Tension is placed on the suture or catheter until it is pulled through the inner wall of the canal, the trabecular meshwork, and into the anterior chamber. This 360-degree procedure is carried out ab externo, through a conjunctival incision and partial thickness scleral dissection to expose Schlemm's canal. When the full 360 degrees of Schlemm's canal cannot be treated, a partial trabeculotomy of greatest length is usually performed, which also provides significant increase in aqueous outflow and reduction in intraocular pressure.

An embodiment of the claimed invention is directed to an ab interno approach to a trabeculotomy utilizing a device such as a microcatheter, a suture, or other device that can be inserted into Schlemm's canal. In embodiments of the invention, the device that is used is flexible in nature. In embodiments of the invention, the lumen of Schlemm's canal is accessed from the anterior chamber without the need or requirement for dissection of the sclera or conjunctiva. This is possible because the inner wall of Schlemm's canal, the trabecular meshwork, is directly adjacent to the anterior chamber.

FIG. 1 shows the structure of the eye in cross-section. The lens (1), iris (2) and cornea (3) are shown. Also shown is the location of the trabecular meshwork (4) and Schlemm's canal (5).

Figure 2:
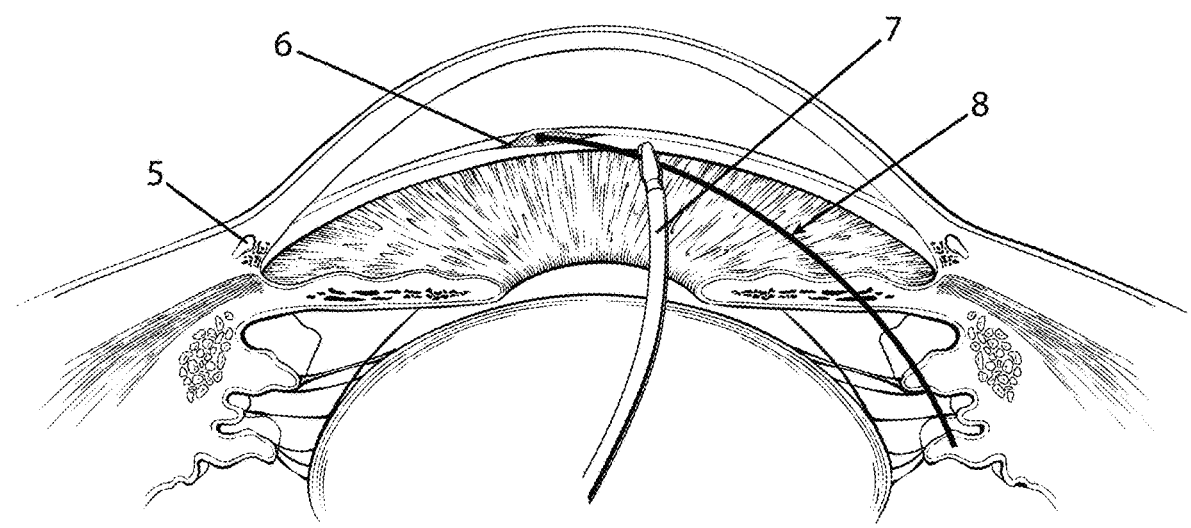
FIG. 2 shows the creation of an incision in the trabecular meshwork of the eye and the insertion of a device into the incision in accordance with an embodiment of the invention.

In an embodiment of the invention, a goniotomy or incision of Schlemm's canal is created using a microsurgical instrument from within the anterior chamber with the aid of a gonioscopy prism or other imaging device to visualize the anterior chamber angle. As shown in FIG. 2, an incision (6) is made in the trabecular meshwork (4) using a cutting instrument (not shown) from within the anterior chamber. A device (8) is used to cannulate the goniotomy opening, i.e., the device is inserted into the goniotomy opening, and enter Schlemm's canal (5).

Figure 3:
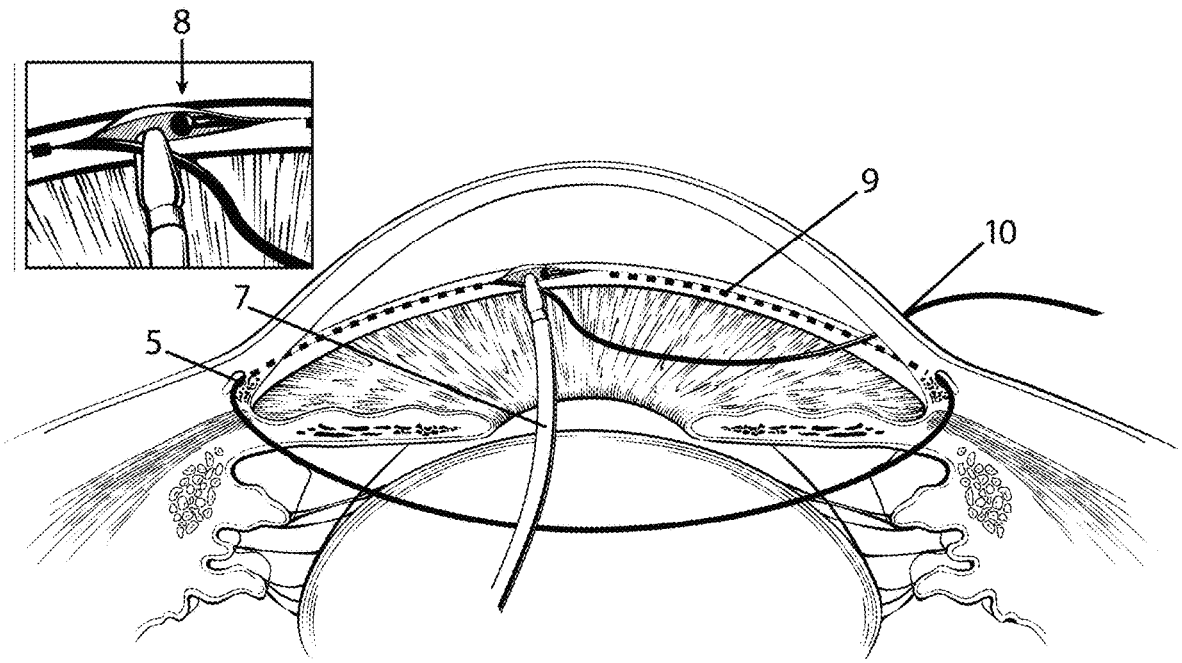
FIG. 3 shows the advancement of a device within Schlemm's canal in accordance with an embodiment of the invention.

As shown in FIG. 3, after entry into Schlemm's canal (5), the device (8) is advanced along the canal. The advancement of the device (8) is facilitated using an instrument (7) that grips the device and advances the device along a path within the canal (9). An instrument such as a forceps, or more specifically an ocular microforceps (7) is used to insert and advance the device (8) into and within Schlemm's canal.

In an embodiment of the invention, an incision is made through the cornea (10) for insertion of the device (8).

Figure 4:
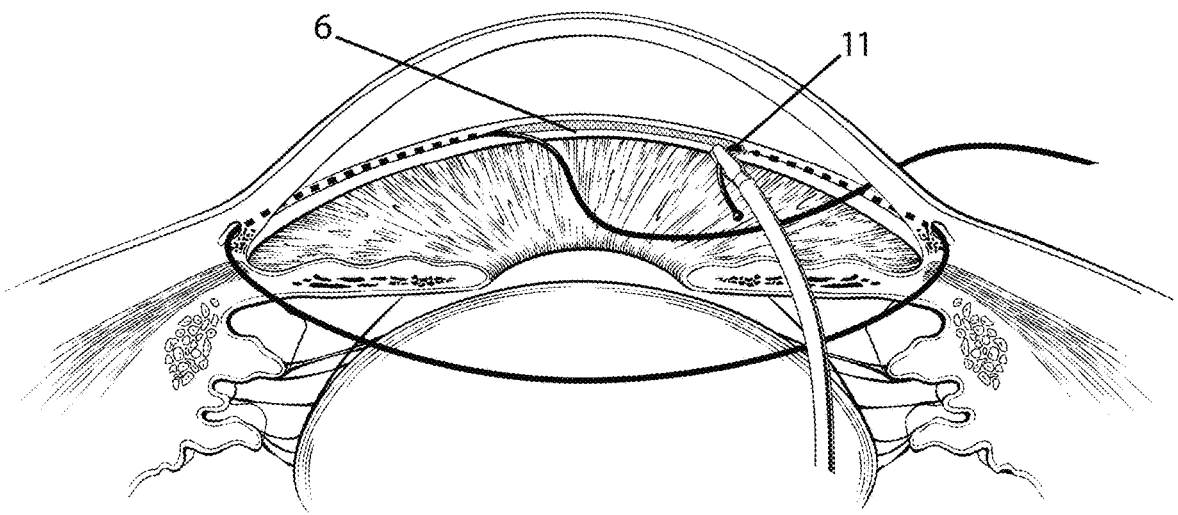
FIG. 4 shows the completion of the trabeculotomy in accordance with an embodiment of the invention.

In an embodiment of the invention, the device (8) is advanced within Schlemm's canal until the distal end of the device is near the initial goniotomy incision, i.e., 360 degrees. The instrument (7) that is used to insert and advance the device (8) through Schlemm's canal is used to retrieve the distal end of the device (8) as shown in FIG. 4. Traction or tension is then placed on the proximal and distal ends of the device using the instrument (7) to pull the device into the anterior chamber, thus rupturing the trabecular meshwork, exposing Schlemm's canal and thereby create a 360-degree trabeculotomy ab interno as shown in FIG. 4 (11).

Due to scarring or malformations of Schlemm's canal, it may not always be possible to advance the device around the complete circumference of the canal. Thus, in certain embodiments of the invention, the trabeculotomy procedure using the inventive method may also be performed on a portion of Schlemm's canal as a partial trabeculotomy by advancing the device partially for one or more clock hours through Schlemm's canal, and then retrieving the distal end through the trabecular meshwork via an incision (goniotomy). Applying tension to one or both ends of the device would then form a partial trabeculotomy between the goniotomy (point of incision and insertion of device) and the distal end.

In certain embodiments of the invention, the trabeculotomy may continue to be applied to the untreated portion of Schlemm's canal by cannulating the remaining portion of the canal and repeating the partial trabeculotomy procedure. For example, the entire canal could be treated by two 180 degree procedures, three 120 degree procedures or any similar combination. In highly compromised or diseased eyes, only a portion of Schlemm's canal may be cannulated and a partial trabeculotomy performed using the technique set forth herein.

In certain embodiments of the invention, the device that is used to cannulate Schlemm's canal comprises a flexible device that is of a suitable size, shape and thickness to enter and cannulate the circumference of the canal. The meridional diameter of Schlemm's canal ranges from 200 to 250 microns and has been reported as large as 350 to 500 microns. The canal has a reported length of 36 mm with some variation due to the size of the eye or from disease conditions. For cannulating Schlemm's canal, the device is preferred to be from approximately 10 to 500 microns in diameter and length of at least 36 mm. To facilitate advancement of the device in the canal, the distal tip may be rounded and the device may have a lubricious coating on at least the distal end. The device may comprise a flexible metal, polymer, or natural material. The device may be straight, or also incorporate a curve at the distal end. The curve may be greater than or approximate the curvature of Schlemm's canal. In certain embodiments of the invention, the curved tip has a radius ranging from 2 to 4 mm. The device may also comprise a lumen such as a microcatheter to allow the delivery of materials from or to the distal tip. In addition, the device may have markings along the length of the device or at the tip to help visualization the device within the canal.

In an embodiment of the invention, the device that is used in methods of the invention comprises a tip which emits light to allow the tip location to be visualized through the trabecular meshwork from within the eye, as well as through the sclera and conjunctiva from outside of the eye to provide guidance for advancement within the canal. Although a light emitting device may be desirable, it is not required for this procedure.

The primary advantage of the presently disclosed ab interno approach is that it does not require a conjunctival or scleral incision. As such, no scleral dissection is required and there is no risk for a bleb on the surface of the eye. Additionally, this approach spares the entire conjunctiva and sclera, which is ideal in the event that traditional glaucoma surgery or other eye surgery is needed in the future. Postoperatively, the recovery time is at least on par with patients who have undergone a 360-degree trabeculotomy ab externo, however, initial experience suggests it is less due to the lack of conjunctival and scleral dissection.

In an embodiment of the invention, a lid speculum is placed in the eye and a gonioprism (or other anterior chamber angle imaging device) is placed on the eye. The surgical microscope is tilted so that the anterior chamber angle at the goniotomy site can be appreciated. In accordance with the embodiment of the invention, the ciliary body structures, the trabecular meshwork, as well as the scleral spur in the anterior chamber angle are identified.

A tangential paracentesis incision is made in the cornea, through which an intraocular composition is injected in order to constrict the pupil and facilitate access to the trabecular meshwork from the anterior chamber. In certain embodiments of the invention, the composition that is used comprises acetylcholine. Examples of such compositions include Miochol-E® and Miostat®.

In accordance with an embodiment of the invention, a surgical viscoelastic such as a solution of sodium hyaluronate is injected into the anterior chamber of the eye to maintain or enlarge the chamber dimensions. Examples of the composition include, but are not limited to Healon®, which is a non-pyrogenic solution of a highly purified high molecular weight fraction of sodium hyaluronate extracted from animal tissue, dissolved in a physiological buffer. The average molecular weight of the sodium hyaluronate in Healon is approximately 4 million Daltons. Following the viscoelastic injection, a clear corneal incision of approximately 1-3 mm in width is made approximately 3 clock hours away from the paracentesis using a microsurgical blade. A different microsurgical blade is inserted into the corneal incision and used to form a goniotomy by incising the trabecular meshwork in the region directly across the eye from the corneal incision to create direct access to the lumen of Schlemm's canal. The device is inserted into the paracentesis and the gonioprism is placed on the eye to visualize the distal end of the device approaching the angle structures in the incised region of the canal. Surgical forceps are then inserted into the eye through the clear corneal incision. These are used to grasp the device and direct the distal part of the device into the incision of Schlemm's canal. The gonioprism (or other device used to image the anterior chamber angle) is placed in or on the eye and allows visualization of this procedure. The device is threaded into Schlemm's canal through the incision created by the microsurgical blade.

The positioning of the device is confirmed through an external view of the eye. In an embodiment of the invention, if a lighted microcatheter is used to cannulate Schlemm's canal, the transillumination of the light at the distal end of the catheter in Schlemm's canal can be visualized internally or externally. If a lighted microcatheter is not used, then the device is visualized directly internally or externally without the aid of a lighted catheter.

In certain embodiments of the invention, a microcatheter may be used to cannulate Schlemm's canal. In such a case, a viscoelastic may be injected into the catheter during advancement in Schlemm's canal to provide lubrication and reduce the force needed for advancement. The injected viscoelastic may also aid the procedure by filling the downstream collector channels and reducing blood reflux into the anterior chamber of the eye.

Following the cannulation of Schlemm's canal, the surgical forceps are placed back into the eye with a gonioprism on the eye for visualization and the device is advanced around the canal. The distal end of the device is retrieved with the surgical forceps and removed from the eye through the clear corneal incision. This creates a 180-degree trabeculotomy in the inferior quadrant. The 360-degree trabeculotomy is then completed by grasping and applying tension to the proximal end to finish the trabeculotomy 180 degrees superiorly. The device is then removed from the eye through the paracentesis.

In accordance with an embodiment of the invention, an endoscopic camera may be used to visualize the surgical procedure within the anterior chamber to facilitate proper placement and use of the instruments within the anterior chamber. Upon completing the trabeculotomy, blood reflux is typically noted from the canal. Surgical viscoelastic is injected into the eye to reform the chamber and maintain adequate pressure with the additional goal of blocking the flow of blood. A single suture such as an interrupted 10-0nylon suture is placed through the clear corneal incision if needed. Prior to tying the suture, the previously injected surgical viscoelastic is irrigated out of the anterior chamber, as is blood that has refluxed into the anterior chamber. The suture is then tied off and the eye pressurized by injection of balanced salt solution to a pressure of at least 10-15 mmHg by palpation.

An intraocular composition such as Miochol-E® is injected into the eye, followed by a subconjunctival injection of prophylactic antibiotic and an anti-inflammatory agent such as a corticosteroid that is administered inferiorly. It is further noted that the wounds are watertight and the pressure is slightly above the physiologic state to minimize the chance of bleeding.

From the foregoing description, it should now be appreciated that a novel approach for the surgical treatment of glaucoma has been disclosed for releasing excessive intraocular pressure. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A method for performing a trabeculotomy of an eye ab interno, the method comprising the steps of:
    making an incision in a cornea to access a trabecular meshwork of an eye;
    making an incision in the trabecular meshwork to access a lumen of a Schlemm's canal of the eye;
    threading a distal tip of a device through the incision and into an interior of the Schlemm's canal;
    pulling the distal tip of the device out of the Schlemm's canal into an anterior chamber of the eye; and
    applying tension to the device within the Schlemm's canal to rupture the trabecular meshwork in an area cannulated by the device.

2. The method of claim 1, wherein the threading comprises advancing the device along a full circumference of the Schlemm's canal.

3. The method of claim 1, wherein the threading comprises advancing the device along the Schlemm's canal for a portion of the Schlemm's canal.

4. The method of claim 1, wherein the device comprises a lumen to inject fluid during cannulation of the Schlemm's canal.

5. The method of claim 1, wherein the device comprises a lighted tip to facilitate visualization of a location of the lighted tip during cannulation of the Schlemm's canal.

6. The method of claim 1, wherein the device comprises a curved tip.

7. The method of claim 6, wherein the curved tip has a radius ranging from 2 to 4 mm.

8. The method of claim 1, further comprising making a second corneal incision to retrieve the distal tip of the device.

9. A method for performing a trabeculotomy of an eye ab interno, the method comprising the steps of:
    making an incision in a cornea to access a trabecular meshwork of an eye;
    making an incision in the trabecular meshwork to access a lumen of a Schlemm's canal of the eye;
    injecting a viscoelastic into the Schlemm's canal;
    threading a distal tip of a device through the incision and into an interior of the Schlemm's canal; and
    applying tension to the device within the Schlemm's canal to rupture the trabecular meshwork in an area cannulated by the device.

10. The method of claim 9, further comprising observing a light emitted by the distal tip as the device is advanced into the Schlemm's canal.

11. The method of claim 9, wherein the incision in the cornea is made at a position of approximately 3 clock hours from a paracentesis for an injection of fluid into the eye.

12. The method of claim 9, wherein the threading comprises advancing the device along a full circumference of the Schlemm's canal.

13. The method of claim 9, further comprising injecting additional viscoelastic into the eye to pressurize the eye.

14. The method of claim 9, wherein the incision in the trabecular meshwork is extended as the distal tip of the device is advanced into the Schlemm's canal.

* * * * *